United States Patent [19]

Ho et al.

[11] Patent Number: 5,149,529

[45] Date of Patent: Sep. 22, 1992

[54] COMPOSITIONS AND TREATMENT FOR HERPES SIMPLEX

[75] Inventors: Rodney Ho, Danville; Thomas Merigan, Portola Valley; Rae L. Burke; Dino Dina, both of San Francisco, all of Calif.

[73] Assignees: Board of Trustees of Leland Chiron Corporation, Emeryville; Stanford Junior University, Stanford, both of Calif.

[21] Appl. No.: 773,073

[22] Filed: Oct. 11, 1991

Related U.S. Application Data

[63] Continuation of Ser. No. 179,095, Apr. 8, 1988, abandoned.

[51] Int. Cl.$^5$ .................................. A61K 39/245
[52] U.S. Cl. .................................. 424/88; 424/89; 424/85.5; 424/452; 514/8
[58] Field of Search ............ 514/8; 424/89, 85.5, 424/88, 450, 452

[56] References Cited

U.S. PATENT DOCUMENTS

| | | | |
|---|---|---|---|
| 4,053,585 | 10/1977 | Allison et al. | 424/92 |
| 4,082,735 | 4/1978 | Jones et al. | |
| 4,082,736 | 4/1978 | Jones et al. | |
| 4,101,536 | 7/1978 | Yamamura et al. | |
| 4,185,089 | 1/1980 | Derrien et al. | |
| 4,235,771 | 11/1980 | Adam et al. | |
| 4,247,411 | 1/1981 | Vanlerberghe et al. | 252/316 |
| 4,261,975 | 4/1981 | Fullerton et al. | 424/89 |
| 4,406,890 | 9/1983 | Tarcsay et al. | 424/177 |
| 4,606,918 | 8/1986 | Allison et al. | |
| 4,618,578 | 10/1986 | Burke et al. | 435/68.3 |
| 4,642,333 | 2/1987 | Person et al. | |
| 4,661,349 | 4/1987 | Kino et al. | |
| 4,766,046 | 8/1988 | Abra et al. | 424/450 |
| 4,897,355 | 1/1990 | Eppstein et al. | 435/240.2 |
| 4,963,354 | 10/1990 | Shepard et al. | 424/85.1 |

OTHER PUBLICATIONS

Koff et al., 1984, *Science*, 224: 1007–1009.
Koff et al., 1985, *Science*, 228: 495–497.
Nakamura et al., 1984, Nature 307: 381–382.
Stanberry et al., (1988) Journal of Infectious Diseases 157(1): 156–163.
Dundarov et al., (1982) Develop. Biol. Standard. 52: 351–358.
Skinner et al., (1982) Develop. Biol. Standard 52: 333–344.

*Primary Examiner*—Robert A. Wax
*Assistant Examiner*—Keith C. Furman
*Attorney, Agent, or Firm*—Grant D. Green; Barbara G. McClung; Roberta L. Robins

[57] ABSTRACT

A method for preventing or ameliorating HSV infection in a bird or mammal comprises administering a composition comprising an effective amount of an HSV surface glycoprotein and an effective amount of an MDP equivalent, encapsulated in liposomes. The resulting composition is useful for reducing the severity and recurrence of HSV outbreaks.

11 Claims, 2 Drawing Sheets

COMPOSITIONS AND TREATMENT FOR HERPES SIMPLEX

This is a continuation of copending application Ser. No. 07/179,095, filed on Apr. 8, 1988, now abandoned.

TECHNICAL FIELD

This invention relates to recombinant DNA technology, to the treatment and prevention of disease, and to compositions therefor. In particular, this invention relates to liposomal formulations of recombinant Herpes virus surface glycoprotein D-1 (HSV rgD-1).

BACKGROUND OF THE INVENTION

The herpes viruses include the herpes simplex viruses, comprising two closely related variants designated types 1 (HSV-1) and 2 (HSV-2). These types cross react strongly, but can be distinguished by neutralization titrations. HSV-1 and HSV-2 are responsible for a variety of human diseases, such as skin infection, genital herpes, viral encephalitis, and the like.

The herpes simplex virus is a double stranded DNA virus having a genome of about 150 to 160 Kb, packaged within an icosahedral nucleocapsid, enveloped in a membrane. The membrane includes a number of virus-specific glycoproteins, the most abundant of which are gB, gC, gD, and gE. The proteins gB and gD are cross-reactive between HSV-1 and HSV-2.

It is a matter of great medical and scientific interest to provide safe and effective vaccines for humans against both HSV-1 and HSV-2, and where infection has occurred, to provide therapies for treatment of the disease. One promising approach has been the use of isolated glycoproteins, which have been shown to provide protection when injected into mice subsequently challenged with live virus. These proteins are produced by, e.g., the methods taught in U.S. Pat. No. 4,618,578, incorporated herein by reference.

Another critical aspect affecting vaccine efficacy is the vehicle employed to deliver the antigen. Proper activation of the immune system depends on a complex series of interactions between the immune system's various components, which include antigen presenting cells (APC), e.g., macrophages, dermal Langerhans cells, and dendritic cells; helper thymocytes ($T_h$-cells); cytotoxic thymocytes ($T_c$-cells); and immunoglobulin-secreting B-cells. APCs ingest foreign particles in the body, partially digest the antigens thereon, and "present" the partially-digested antigens on their surfaces in association with proteins encoded in the major histocompatability complex (MHC) genes. MHC proteins are classified as type I (which are expressed on the surfaces of all nucleated cells), and type II, which are expressed only on certain cells of the immune system. Type II proteins are interchangeably denoted as MHC Ia (for "immune-associated"). APCs express both MHC I and Ia, but it is the Ia-antigen complexes that are important for initial activation of the immune system. These antigen-MHC Ia complexes are recognized by $T_h$ cells that bear a T-cell receptor capable of binding to the complex. This binding, in addition to the secretion of certain cytokines (particularly interleukin-1, "IL-1"), effects activation of the $T_h$ cell. As a result, the stimulated $T_h$ cells proliferate and begin secreting other cytokines, eventually activating $T_c$ cells and B-cells specific for the antigen that originally started the cascade. $T_c$ cells recognize antigen in combination with MHC I proteins on cell surfaces, and effect lysis of such cells in a process known as cell mediated immunity (CMI) Thus, $T_c$ cells and CMI are believed to be particularly important in the immune response to viral infection, as lysis of cells exhibiting viral antigens results in interruption of viral reproduction.

B-cells express antibodies of the various classes in a process known as humoral immunity. The antibody classes most important in resistance to infection are IgM, IgG, and IgA. Antibodies may also play a role in protection from viral infection, by fixing complement on infected cells, by clearing viral particles from the bloodstream, by opsonizing cells for clearance by macrophages and neutrophils, and by initiating antibody-dependent cell-mediated immunity (ADCC), which is effected by killer cells (K).

The efficacy of these immune defenses varies depending upon the pathogen's antigenicity and mode of infection. When designing a vaccine, the object is to provide for activation of those immune defenses which will result in the most effective protection from the pathogen in question. In general, an adjuvant is often employed in order to increase the immune response to a particular antigen. Most adjuvants, however, are only able to enhance humoral immunity, and fail to increase cell mediated immunity.

The mode of administration is also of critical importance. Most vaccines are administered intramuscularly or subcutaneously (in rare cases intradermally), as lymph in these tissues drains into the lymph nodes where the antigens will be accessible to $T_h$ cells and macrophages. In contrast, administration of soluble antigens by intravenous routes may result in tolerance to the antigen, i.e., a suppression of any immune response.

The archetypal adjuvant is Freund's adjuvant, which is commonly used in laboratory immunology. Freund's complete adjuvant (FCA) consists of an oil-in-water emulsion of mineral oil, surfactant, and killed mycobacteria (*M. tuberculosis*). Freund's incomplete adjuvant (FIA) omits the mycobacteria. These adjuvants provide an enhanced immune response, but are not suitable for administration to humans, as mycobacteria are the causative agent of tuberculosis, and may cause adverse responses detrimental to the subject. Further, the mineral oil component is not metabolized, and may cause abscesses and granulomas at the site of injection. Researchers have since replaced the mycobacteria with muramyl dipeptide (MDP) derivatives, which were determined to be the smallest component of the mycobacterial cell walls that retained the adjuvant activity. The preparation of various MDP derivatives and analogs is described in detail in U.S. Pat. Nos. 4,082,735; 4,082,736; 4,101,536; 4,185,089; 4,235,771; and 4,406,890. It is currently believed that the MDP derivative stimulates the release of IL-1. The mineral oil component has been replaced by various synthetic and metabolizable vegetable oils. See for example Allison et al, U.S. Pat. No. 4,606,918, disclosing an adjuvant formulation comprising muramyl dipeptide, a polyoxypropylene-polyoxyethylene block polymer (Pluronic®), a non-ionic surfactant, and a metabolizable oil such as squalane. Other adjuvants known in the art include alum, lipid A, trehalose dimycolate, and dimethyldioctadecylammonium bromide (DDA). However, only alum has been approved for human administration.

Liposomes have also been employed to deliver biologically active material. See for example Allison, U.S.

Pat. No. 4,053,585, which discloses the administration of several antigens in negatively-charged liposomes, optionally including killed *M. tuberculosis*. Fullerton et al, U.S. Pat. No. 4,261,975, discloses the use of separated influenza membranes, with hemagglutinin spikes attached, which is bound to liposomes for use in influenza vaccines. Tarcsay et al, U.S. Pat. No. 4,406,890, discloses the use of liposomes to encapsulate MTP-PE (a lipophilic MDP derivative) and bovine serum albumin (a standard model antigen). Liposomes are small vesicles composed of amphipathic lipids arranged in bilayers. Liposomes are usually classified as small unilamellar vesicles (SUV), large unilamellar vesicles (LUV), or multi-lamellar vesicles (MLV). SUVs and LUVs have only one bilayer, whereas MLVs contain many concentric bilayers. Liposomes may be used to encapsulate various materials, by trapping hydrophilic compounds in the interior or between bilayers, or by trapping hydrophobic compounds in the bilayer.

Liposomes exhibit a wide variety of characteristics, depending upon their size, composition, and charge. For example, liposomes having a small percentage of unsaturated lipids tend to be slightly more permeable, while liposomes incorporating cholesterol tend to be more rigid and less permeable. Liposomes may be positive, negative, or neutral in charge, depending on the hydrophilic group. For example, choline-based lipids impart a positive charge, phosphate and sulfate based lipids contribute a negative charge, and glycerol-based lipids tend to be neutral in solution.

Several HSV vaccines have been prepared. S. Dundarov et al, *Dev Biol Standard*, 52:351–57 (1982) disclosed the treatment of humans with formalin-inactivated HSV in distilled water. GRB Skinner et al, *Dev Biol Standard*, 52:333–44 (1982) disclosed the treatment of humans with formalin-inactivated HSV in saline. L. Chan, *Immunol*, 49:343–52 (1983) disclosed the protective immunization of mice against HSV challenge by vaccination with gD in saline. Kino et al, U.S. Pat. No. 4,661,349 disclosed vaccines comprising purified HSV gB with alum. Person, U.S. Pat. No. 4,642,333 disclosed HSV gB and its administration to rabbits in Freund's adjuvant. Recently, L.R. Stanberry et al, *J Infect Dis*, 157:156–163 (1988) reported the use of rgD and rgB in a vaccine to ameliorate the symptoms of genital herpes infection in guinea pigs.

DISCLOSURE OF THE INVENTION

The instant invention comprises a method for treating infection in an individual infected with HSV-1 and/or HSV-2, by parenterally administering a composition comprising an HSV surface glycoprotein and an MDP equivalent, encapsulated in liposomes in aqueous suspension. Presently preferred glycoproteins are gB1, gD1, gB2, gD2, and derivatives thereof. Most preferred is rgD-1.

Another aspect of the invention is the composition suitable for effecting treatment of HSV infection, which comprises an effective amount of an HSV surface glycoprotein (preferably rgD-1), an effective amount of an MDP equivalent, encapsulated in liposomes in aqueous suspension.

Another aspect of the invention is a lyophilized composition comprising an HSV surface glycoprotein (preferably rgD-1), an MDP equivalent, and liposome-forming lipids, which is capable of forming liposomes upon hydration.

MODES OF CARRYING OUT THE INVENTION

A. Definitions

Figure 1:
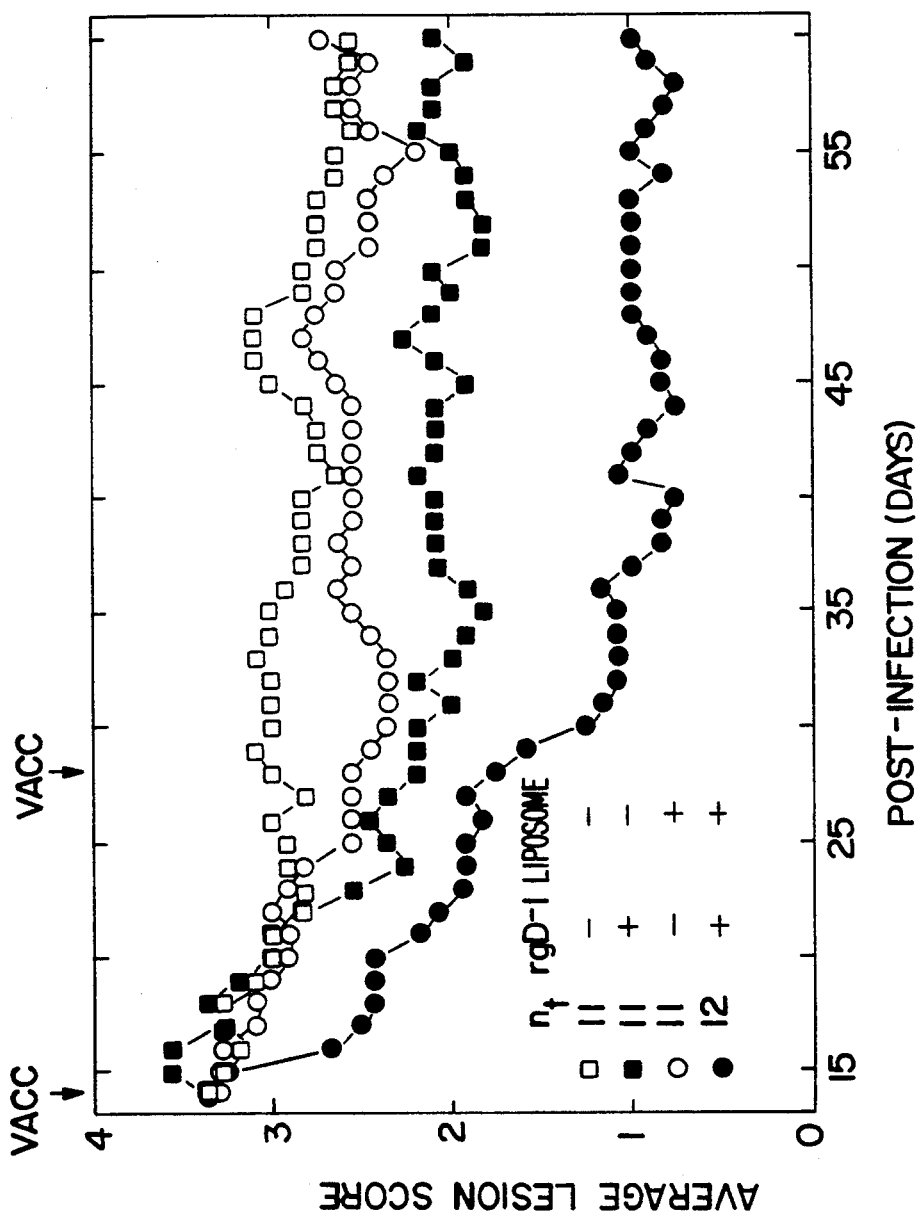
FIG. 1 depicts a plot of HSV-2 lesion severity vs. time for four experimental groups of animals.

The term "HSV glycoprotein" refers to any of the glycoproteins found in the membrane region of HSV-1, HSV-2, and related herpes viruses. Presently preferred HSV glycoproteins are gB, gC, gD, and gE. Included within this definition are glycoproteins extracted from natural viruses (e.g., from infected sera or cell culture), and glycoproteins produced by recombinant methods. Such glycoproteins may additionally be modified, either by chemical or enzymatic means (e.g., by proteolytic cleavage), or by recombinant DNA techniques (e.g., by fusing HSV glycoprotein genes with other genes to provide fusion proteins, or by deleting or replacing sections of the DNA sequence).

The term "rgD-1" refers to a recombinantly-produced HSV surface glycoprotein D1, which is truncated at the carboxy terminus and lacks the hydrophobic membrane anchor and cytoplasmic domains of the native protein. After removal of the signal peptide in CHO cells, the resulting protein is 290 amino acids in length.

The term "MDP equivalent" refers to any of the commonly known compounds chemically related to N-acetylmuramyl-L-alanyl-D-isoglutamine (MDP), and capable of eliciting IL-1 expression in vivo. Appropriate MDP equivalents include, without limitation, MDP itself, N-acetylmuramyl-L-threonyl-D-isoglutamine ("Thr-MDP"), N-acetyl-nor-muramyl-L-alanyl-D-isoglutamine ("Nor-MDP"), n-butyl N-acetylmuramyl-L-alanyl-D-isoglutaminate (murabutide), N-acetylmuramyl-L-alanyl-D-isoglutaminyl-L-alanyl-2-[1,2-dipalmitoyl-sn-glycero-3-(hydroxyphosphoryloxy)]-ethylamide (MTP-PE), and the like. Other MDP eqivalents, for the purposes of this invention, include gamma interferon, IL-1, granulocyte-monocyte colony stimulating factor (GM-CSF), and monocyte colony stimulating factor (M-CSF).

The term "treatment" as used herein refers any of (i) the prevention of infection or reinfection (prophylaxis), (ii) the reduction or elimination of symptoms, and (iii) the substantial elimination of the virus.

The term "effective amount" refers to the amount of rgD-1 sufficient to induce an immune response in a recipient subject when administered in the composition of the invention. The immune response is preferably protective immunity, whether this is achieved by humoral immunity, cell mediated cytotoxicity, or other mechanisms. "Effective amount" also refers to the amount of MDP equivalent necessary to potentiate the subject's immune response to the antigen.

B. General Method

HSV rgD antigens may be prepared by the method set forth in U.S. Pat. No. 4,618,578, incorporated herein by reference. Briefly, the HSV gene encoding gD is cloned in a shuttle vector suitable for modification and amplification in a prokaryotic host (e.g., *E. coli*) and for expression in a eukaryotic vector. Standard microbiological techniques are employed to provide suitable promoter and termination regions for the gD gene, and selectable markers for the vector, in order to allow control of gD expression in the expression host. The gD gene may be supplemented with nucleotides encoding other regulatory and functional sequences, for example for secretory signal peptides, or for leader cleavage by endogenous enzymes. One may also delete segments of the gD gene: for example, one may delete the hydrophobic membrane anchor domain to improve the solubility of the protein. The rgD-1 protein preferred herein is truncated at the carboxy terminus, and is lacking both the membrane anchor and the cytoplasmic domain.

Preferably, the rgD-1 protein is expressed in Chinese hamster ovary (CHO) cells. The protein is extracted and purified from the cell culture medium by ammonium sulfate precipitation, immunoaffinity chromatography, and ultrafiltration.

MDP equivalents are prepared by methods known to those of ordinary skill in the art. For example, MDP, Nor-MDP, and Thr-MDP may be prepared following the procedures set forth in Jones et al, U.S. Pat. Nos. 4,082,735 and 4,082,736, incorporated herein by reference. Murabutide may be prepared following the procedures set forth in Derrien et al, U.S. Pat. No. 4,185,089, incorporated herein by reference. MTP-PE is prepared following the procedures set forth in Tarscay et al, U.S. Pat. No. 4,406,890, incorporated herein by reference.

Liposomes may be prepared by a large variety of methods. The simplest method comprises evaporating the solvent from a chloroform solution of lipids, leaving a lipid film on the inner surface of the vessel. An aqueous solution (usually lacking Mg++ and Ca++ ions) is then added and agitated (e.g., by vortexing) to form liposomes. Other methods involve adding lipids to aqueous solution with sonication, injection of lipid solutions into aqueous solution with evaporation of co-solvents, or use of special equipment.

In the instant case, we have achieved high capture efficiency by the following process: a mixture of lipids, preferably egg phosphatidylcholine (EPC) and phosphatidylglycerol (PG) in a 9:1 ratio, and MTP-PE (in an amount equal to the PG) is dried under a stream of $N_2$, and vacuum desiccated for 30 minutes. The lipids are then hydrated with sterile water and phosphate-buffered saline (PBS), vortexed, then sonicated for 15 minutes to provide a translucent liposomal suspension. The suspension is then sterile filtered, the antigen added, and the mixture frozen and lyophilized overnight. For use, the lyophilized material is rehydrated, vortexed, and allowed to stand, providing an injectible suspension of SUV liposomes. Capture efficiency is estimated at 47%.

The composition is administered parenterally, usually by intramuscular or subcutaneous injection. One may also administer the composition by intravenous routes, if desired. The precise amount of composition administered will of course depend upon the size, age, and health of the subject, the extent and severity of the disease, and the exact nature of the components used in preparing the composition, hence it is not possible to provide an exact dosage. However, an effective amount of rgD-1 for a 70 Kg adult human ranges from about 10 ug/dose to about 100 ug/dose, preferably about 25 ug–50 ug/dose. An effective amount of MTP-PE ranges from about 1 ug/dose to about 100 ug/dose, preferably about 20 ug/dose. The amount of lipids used is not particularly critical, but a convenient range is about 0.05 mg–3.0 mg/dose. The precise dosage may determined by one of ordinary skill in the art. The composition may be administered in stages, as is typical for vaccines; i.e., an initial administration is followed two to six weeks later by additional "booster" administrations, in order to effect a lasting immunity.

C. EXAMPLES

The examples presented below are provided as a further guide to the practitioner of ordinary skill in the art, and are not to be construed as limiting the invention in any way.

EXAMPLE 1

Preparation of rgD-1

The preferred antigen of the invention, a 290 amino acid truncated gD protein, is prepared as described below.

Cloning and Expression of rgD-1

A library of EcoRI restriction fragments of HSV-1, strain Patton, were cloned into the EcoRI site of the plasmids pBR322 or pACY184 (obtained from Dr. Richard Hyman, Hershey Medical Center, Hershey, Pa.). The gD1 gene, which is entirely contained within a 2.9 Kb SacI fragment within the EcoRI fragment of clone H from this library, was obtained by restriction digestion, purified by gel electrophoresis, and digested to completion with HindIII and NcoI. The 5' end of the gD gene, consisting of 74 bp of 5' untranslated sequence plus 60 bp encoding the amino terminal 20 amino acids, was isolated as a 134 bp HindIII/NcoI fragment. A portion of the 3' end of the gD gene was obtained by digestion of pYHS119 (described in U.S. Pat. No. 4,618,578, incorporated herein by reference) with NcoI and SalI and isolation of the 873 bp fragment. These two fragments (5' and 3' ends) were ligated together with the plasmid pUC12 (previously digested with HindIII and SalI). The resulting plasmid was digested with HindIII, the sticky ends filled in with Klenow fragment (DNA polymerase I), and digested with SalI. The 1007 bp fragment containing the gD gene was isolated and ligated into the mammalian expression vector pSV7d, previously cut with SmaI and SalI (see R.L. Burke et al, *J Biol Chem*, 261:12574 (1986)). The resulting plasmid (designated pHS132) encodes 315 amino acids out of a total of 394 for the complete gD1 protein (including the 25 amino acid signal sequence). The resulting protein is truncated at the carboxy terminus, and lacks the hydrophobic membrane anchor domain and the cytoplasmic domain. After cleavage of the signal sequences, a 290 amino acid protein (rgD-1) is secreted into the culture medium.

The rgD-1 expression vector pHS132 is cotransfected into CHO cells with the Ad-dhfr plasmid which encodes the selectable and amplifiable marker gene dihydrofolate reductase (DHFR). DHFR-positive clones were screened for synthesis and secretion of rgD-1 with an ELISA, and the most productive cell line propagated in roller bottles.

Purification

The rgD-1 truncated protein was isolated from the conditioned medium as follows:

Culture medium (300 mL) was acidified to pH 4.5 by adding 15 mL 1M citrate (pH 3.0), and allowed to stand for 10 minutes at 4° C. The acidic medium was brought to 1M $(NH_4)_2SO_4$ by adding 462 g of solid $(NH_4)_2SO_4$. The precipitate was removed by centrifugation at 5,000 rpm at 4° C. for 10 minutes. Next, 300 mL of supernatant was applied to a 15 mL column of fast flow Phenyl Phenyl "SEPHAROSE" ("SEPHAROSE"—O—CH$_2$—CHOH—CH$_2$—O—C$_6$H$_5$, Sigma Chemical Co.) at pH 4.6, and eluted with a 30 minute linear gradient from 1M (NH$_4$)$_2$SO$_4$, 0.5M sodium acetate, pH 4.6 to 0.05M sodium acetate, pH 4.6. Peak fractions were identified by ELISA and were pooled. The pooled fractions were dialyzed into 0.02M sodium acetate, pH 6, and loaded onto a 5 mL "BIOGEL" TSK SP 5 PW cation exchange column (Biorad). Elution was achieved with a 60 minute gradient from 0.02 sodium acetate, pH 6.0 to 0.5M NaCl, 0.02 sodium acetate, pH 6.0. Peak fractions were identified by ELISA, analyzed by SDS PAGE, and pooled based on gel purity. Pooled fractions were then concentrated to 0.5 mL by pressure filtration and applied to a 25 mL SUPEROSE 12 GPC column equilibrated with 0.1M (NH$_4$)$_2$CO$_3$, pH 7.0. Peak fractions were identified by ELISA and by SDS-PAGE, and were pooled and stored at −20° C.

EXAMPLE 2

Preparation of Liposomal Suspension

A mixture of lipids (2.0 mg), consisting of egg phosphatidylcholine, phosphatidylglycerol, and MTP-PE in a 9:1:1 ratio, was dried under a stream of N$_2$ and desiccated in a vacuum desiccator for 30 minutes. The lipids were then resuspended in injection water (2 mL) with sterile PBS (10 uL). The suspension was vortexed briefly, then sonicated for 15 minutes, providing a translucent liposome suspension. The suspension was passed through a 0.2 u filter for sterilization. Next, rgD-1 (120 ug) was added to the suspension (osmolar equivalent to 0.1 PBS), and the mixture frozen and lyophilized in a Vitus overnight.

Before administration, the lyophilized material was rehydrated in injection water (0.2 mL), vortexed, and allowed to stand at room temperature for 15 minutes. Then, 1.8 mL of injection grade saline is added, providing enough suspension for 4 doses of 0.5 mL (30 ug rgD-1).

EXAMPLE 3

Demonstration of Immunogenicity

Female Hartley strain Guinea pigs (400–500 g, Trents, Modesto Calif.) were divided into groups and administered 8.0 ug rgD-1 in one of the following vehicles:

A. Complete Freund's adjuvant (Sigma Chemical Co.) emulsified with PBS (boosted with incomplete Freund's adjuvant (Sigma Chemical Co.) in PBS (100 uL)
B. 10% alum, 100 mM "TRIZMA" hydrochloride (Tris[hydroxymethyl]aminomethane hydrochloride, Sigma Chemical Co.) (100 uL)
C. 50 ug Thr-MDP, 2.5% "PLURONIC L-121" (polyoxypropylene-polyoxyethylene block polymer, Syntex) 5% squalane, PBS (100 uL)
D. 50 ug Nor-MDP, 40% squalene, 10% ARLACEL A (mannide monooleate, Sigma Chemical Co.), PBS (100 uL)
E. 50 ug MTP-PE, 12.5 mg liposomes (7:3 phosphatidylcholine:phosphatidylserine), PBS (175 uL)
F. 50 ug MTP-PE, 4% squalene, 0.008% "TWEEN 80" (polyoxyethylenesorbitan monooleate, Sigma Chemical Co.), PBS (200 uL)
G. 50 ug MTP-PE, 40% squalene, 10% ARLACEL A (mannide monooleate, Sigma Chemical Co.) PBS (200 uL)
H. 62.5 ug RIBI (RIBI Vaccine Supply Co.) components, 2% squalene-Tween ®80, PBS (250 uL).

All vehicles were administered in the hind footpad. Three administrations were performed at week 0, week 3, and week 6. The animals were bled for antibody determination on weeks 7 and 11.

Antibodies in the Guinea pig serum specific for rgD-1 were measured using an ELISA, using rgD-1 as the coating antigen. Antigen was diluted to a final concentration of 5 ug per well with PBS, and was adsorbed to the wells of a 96-well polyvinylchloride microtiter plate (Dynatech, Alexandria Va.). The plates were washed three times with PBS supplemented with 1% rabbit serum and 0.3% "TWEEN 20" (polyoxyethylenesorbitan monolaurate, Sigma Chemical Co.). Test sera were diluted serially with five-fold dilutions in the wash buffer, and incubated in the antigen-coated wells. All incubations were done for one hour, at 50 uL per well. The plates were again washed, and horseradish peroxidase-conjugated rabbit anti-guinea pig immunoglobulin (Boehringer Mannheim Biochemical, Indianapolis, Ind.) diluted 1:200 in wash buffer was added. Plates were washed with PBS and developed with 1 mg/mL "ABTS" (2,2'-Azinobis(3-ethylbenzthiazolinesulfonic acid), Boeringer Mannheim) (Boehringer Mannheim) in 0.1 M citric acid, pH 4.0, with 0.003% H$_2$O$_2$. The color reaction was stopped after five minutes by the addition of 50 uL of 10% sodium dodecyl sulfate (SDS). The reported titer corresponds to the reciprocal of the dilution which produced an absorption at 414 nm equal to 50% of the maximum absorbance value of each serum.

The results were as follows:

| Group | N | Titer1 | % CFA | Titer2 | % CFA |
|---|---|---|---|---|---|
| | | First Test | | | |
| A | 5 | 15,066 ±2,878 | 100 | 16,834 ±5,527 | 100 |
| B | 4 | 1353 ±318 | 9 | 1118 ±211 | 7 |
| C | 6 | 9641 +1696 | 64 | 7271 +1524 | 43 |

N is the number of animals per group
Titer1 is the Ab titer at week 7
Titer2 is the Ab titer at week 11
% CFA compares B, C titer vs group A (CFA)

| Group | N | Titer1 | % CFA | Titer2 | % CFA |
|---|---|---|---|---|---|
| | | Second Test | | | |
| A | 6 | 13,962 ±2,307 | 100 | 8,298 ±896 | 100 |
| D | 6 | 10,387 ±2,964 | 74 | 5,759 +920 | 69 |
| E | 6 | 9,898 ±1,161 | 72 | 2,653 ±457 | 32 |
| | | Third Test | | | |
| A | 4 | 13,470 ±4,218 | 100 | 12,906 ±2,105 | 100 |
| H | 6 | 13,994 ±4,157 | 104 | 7,833 ±3,946 | 61 |

| Group | N | Titer1 | % Ribi | Titer2 | % CFA |
|---|---|---|---|---|---|
| | | Fourth Test | | | |
| H | 4 | 8,000 ±1,271 | 100 | 1,318 ±310 | 100 |
| F | 5 | 17,072 ±3,457 | 213 | 2,455 ±535 | 186 |
| G | 4 | 14,731 ±3,860 | 184 | 1,181 ±433 | 90 |

These results indicate that rgD-1 is immunoreactive when delivered in an appropriate vehicle.

EXAMPLE 4

Demonstration of Protection

Administration

Hartley strain female guinea pigs (250-300 g, EZH caviary) were divided into treatment groups as follows:
A. placebo (PBS), administered IM in hind leg
B. 12 ug HSV-1 rgD BIOCINE (HSV-gD-1 vaccine formula from Chiron Corp.), administered IM in hind leg
C. 0.2 mL liposomes (no antigen), administered by intra-cardial puncture (with anesthesia)
D. 12 ug rgD-1 in 0.2 mL liposomes, (administered by intra-cardial puncture with anesthesia)

Animals were challenged with $10^4$ pfu HSV-2 administered intravaginally with a ball-tipped needle on day 0, and treated with one of the above formulations on days 14 and 28. Animals were bled on days 0, 14, 28, and 42.

CMI Assay

Peripheral blood lymphocytes were isolated from guinea pig blood by "FICOLL" (a nonionic synthetic polymer of sucrose, Sigma Chemical Co.) gradient centrifugation. After washing the cells with tissue culture fluid, $2 \times 10^5$ cells were suspended with antigen and allowed to grow for 6 days. Triplicate samples were then pulsed with $^3$H-thymidine for 6 hours on the sixth day, and the cells harvested with a cell harvester. Stimulation with phytohemagglutin (PHA) was used as the positive control, and results expressed as $^3$H-dT uptake Ag/mock Ag (mock Ag=supernatant from cell cultures not exposed to HSV). The results were as follows:

| Group | N  | LPI[28]      | % Pos | N  | LPI[42]     | % Pos |
|-------|----|--------------|-------|----|-------------|-------|
| A     | 10 | 3.5 ± 1.7    | 60%   | 10 | 4.5 ± 2.9   | 60%   |
| B     | 10 | 3.6 ± 3.2    | 40%   | 10 | 4.6 ± 3.2   | 70%   |
| C     | 11 | 10.4 ± 13.0  | 73%   | 10 | 4.9 ± 4.7   | 60%   |
| D     | 6  | 8.4 ± 2.8    | 100%  | 5  | 6.9 ± 2.8   | 100%  |

N = number of animals per group
LPI[28] and LPI[42] are the lymphocyte proliferation indices at 28 and 42 days, calculated as the ratio of $^3$H-dT incorporation for test group/$^3$H-dT for mock antigen, reported as average and standard deviation.
% Pos = % of animals in group with LPI ≥ 3 (positive CMI response).

The results demonstrate substantial increase in thymocyte proliferation, which is known to correlate with cell mediated immunity.

Histological Response

The animals were observed daily beginning with day 15, and any lesions graded on a 1-4 scale. The lesions are scored as follows: 1=no apparent lesion, 2=inflammation with vesicle formation, 3=severe inflammation with vesicles forming extended plaques, 4=tissue necrosis. The scores were recorded as averages for each group. The results are shown in FIG. 1, showing group A (open squares), group B (filled squares), group C (open circles) and group D (filled circles). The results indicate that the compositions of the invention are effective for substantial amelioration of symptoms from severe HSV-2 infection.

Episode Recurrence

Figure 2:
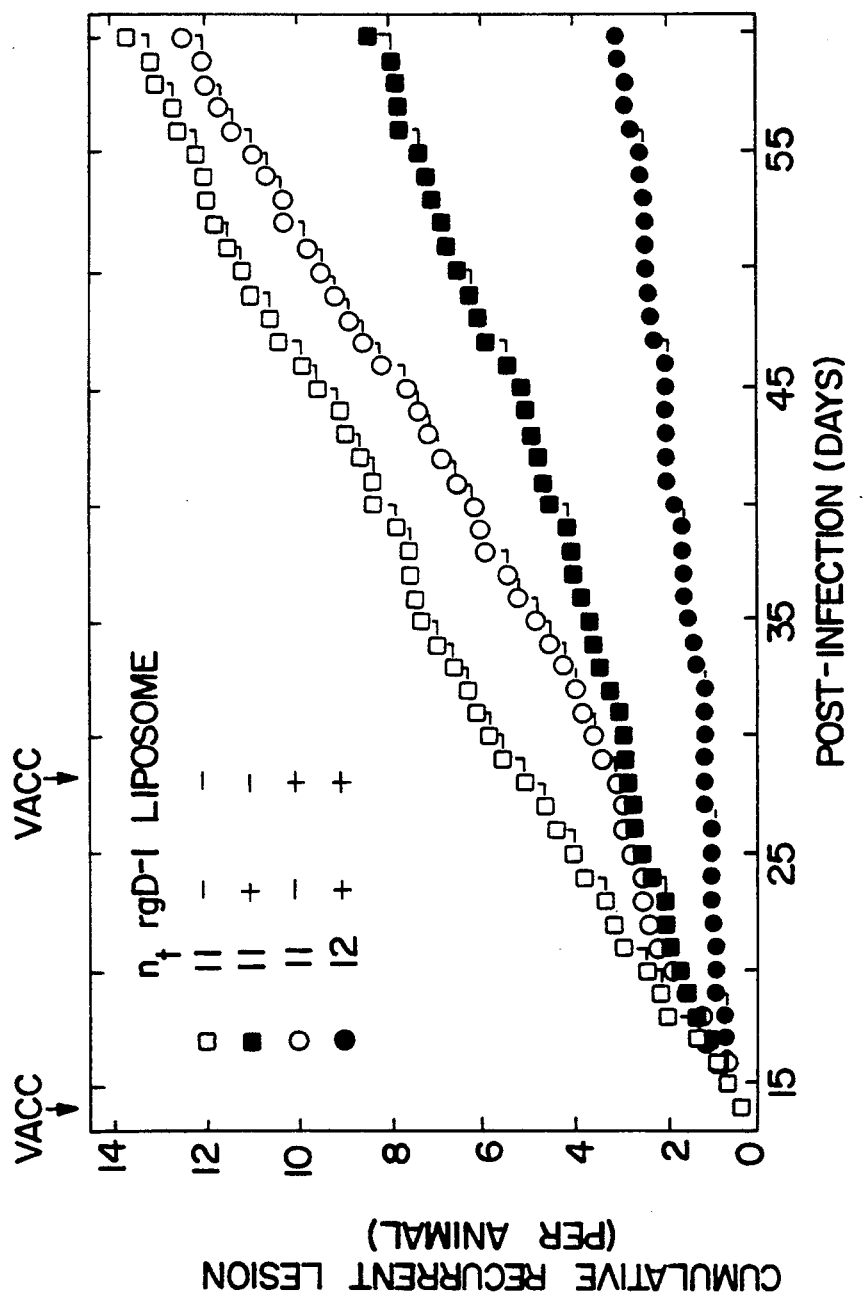
FIG. 2 depicts a plot of cumulative HSV episode recurrence for four experimental groups of animals.

Animals were also observed daily for recurrences of HSV outbreaks. The cumulative total is plotted in FIG. 2, showing group A (open squares), group B (filled squares), group C (open circles) and group D (filled circles). The results indicate that the compositions of the invention substantially reduce the rate of recurrence.

What is claimed:

1. A composition for treating a subject for herpes simplex virus infection, which composition comprises:
   an effective amount of a herpes surface glycoprotein selected from the group consisting of gB and gD; and
   an effective amount of an adjuvant selected from the group consisting of N-acetylmuramyl-L-alanyl-D-isoglutamine and chemical equivalents of N-acetylmuramyl-L-alanyl-D-isoglutamine; wherein said glycoprotein and adjuvant are encapsulated in liposomes in aqueous solution.

2. The composition of claim 1 wherein said surface glycoprotein is selected from the group consisting of rgD-1, rgD-2, rgB-1, and rgB-2.

3. The composition of claim 1 wherein said herpes surface glycoprotein is rgD-1 and said adjuvant is selected from the group consisting of N-acetylmuramyl-L-alanyl-D-isoglutamine, N-acetylmuramyl-L-threonyl-D-isoglutamine, N-acetyl-desmethyl-muramyl-L-alanyl-D-isoglutamine, N-acetylmuramyl-L-alanyl-D-isoglutaminyl-L-alanyl-2-(1,2-dipalmitoyl-sn-glycero-3-(hydroxyphosphoryl-oxy))-ethylamide, and murabutide.

4. The composition of claim 3 wherein said adjuvant is N-acetylmuramyl-L-alanyl-D-isoglutaminyl-L-alanyl-2-(1,2-dipalmitoyl-sn-glycero-3-(hydroxyphosphoryl-oxy))-ethylamide.

5. A composition for reconstitution into a liposomal suspension for the treatment of herpes virus infections, which composition comprises:
   a lyophilized mixture of lipids and an adjuvant selected from the group consisting of N-acetylmuramyl-L-alanyl-D-isoglutamine and chemical equivalents of N-acetylmuramyl-L-alanyl-D-isoglutamine, and a herpes simplex virus surface glycoprotein selected from the group consisting of gB and gD.

6. The composition of claim 5 wherein said surface glycoprotein is selected from the group consisting of rgD-1, rgD-2, rgB-1, and rgB-2.

7. A method for treating herpes simplex virus infection in a mammal, which method comprises:
   administering an effective amount of a composition comprising an effective amount of a herpes surface glycoprotein selected from the group consisting of gB and gD and an effective amount of an adjuvant selected from the group consisting of N-acetylmuramyl-L-alanyl-D-isoglutamine and chemical equivalents of N-acetylmuramyl-L-alanyl-D-isoglutamine, encapsulated in liposomes in aqueous suspension.

8. The method of claim 7 wherein said surface glycoprotein is selected from the group consisting of rgD-1, rgD-2, rgB-1, and rgB-2.

9. The method of claim 7 wherein said adjuvant is selected from the group consisting of N-acetylmuramyl-L-alanyl-D-isoglutamine, N-acetylmuramyl-L-theronyl-D-isoglutamine, N-acetyl-desmethylmuramyl-L-alanyl-D-isoglutamine, N-acetylmuramyl-L-alanyl-D-isoglutaminyl-L-alanyl-2-(1,2-dipalmitoyl-sn-glycero-3-(hydroxyphosphoryl-oxy))-ethylamide, and murabutide.

10. The method of claim 4 wherein said adjuvant is N-acetylmuramyl-L-alanyl-D-isoglutaminyl-L-alanyl-2-((1,2-dipalmitoyl-sn-glycero-3-(hydroxyphosphoryl-oxy))-ethylamide.

11. The composition of claim 5 wherein said mixture comprises egg phosphatidylcholine, phosphatidylglycerol, and N-acetylmuramyl-L-alanyl-D-isoglutaminyl-L-alanyl-2-[1,2-dipalmitoyl-sn-glycero-3-(hydroxyphosphoryl-oxy)]-ethylamide in a 9:1:1 ratio.

* * * * *

UNITED STATES PATENT AND TRADEMARK OFFICE
CERTIFICATE OF CORRECTION

PATENT NO.  : 5,149,529
DATED       : September 22, 1992
INVENTOR(S) : Rodney Ho, Danville; Thomas Merigan, Portola Valley; Rae L. Burke; Dino Dina, both of San Francisco, all of California It is certified that error appears in the above-identified patent and that said Letters Patent is hereby corrected as shown below:

ON THE TITLE PAGE:

[73] Assignees: <u>Delete</u>: "Board of Trustees of Leland Chiron Corporation, Emeryville; Stanford Junior University, Stanford, both of Calif."

[73] Assignees: <u>Correct</u>: --Chiron Corporation, Emeryville; Board of Trustees of Leland Stanford Junior University, Stanford; both of California.--

Signed and Sealed this

Twelfth Day of October, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,149,529
DATED : September 22, 1992
INVENTOR(S) : Rodney Ho et al

It is certified that error appears in the above-indentified patent and that said Letters Patent is hereby corrected as shown below:

Column 1, after Line 6, and before "Technical Field":

add:

"This invention was made with Government support under contract AI05629-24 awarded by the National Institutes of Health. The Government may have certain rights in this invention."

Signed and Sealed this

Seventh Day of November, 1995

Attest:

BRUCE LEHMAN

*Attesting Officer*     *Commissioner of Patents and Trademarks*